United States Patent [19]

Simon

[11] Patent Number: 6,103,258
[45] Date of Patent: Aug. 15, 2000

[54] SALTS AND BASES OF THE 17-(CYCLOPROPYLMETHYL)-4,5 ALPHA-EPOXY-6-METHYLENEMORPHINAN-3,14 DIOL MOLECULE FOR OPTIMIZING DOPAMINE HOMEOSTASIS DURING ADMINISTRATION OF OPIOID ANALGESICS

[76] Inventor: David Lew Simon, P.O. Box 618, Mansfield Center, Conn. 06250

[21] Appl. No.: 09/111,068

[22] Filed: Jul. 7, 1998

Related U.S. Application Data

[63] Continuation-in-part of application No. 08/631,081, Apr. 12, 1996, Pat. No. 5,783,583.

[51] Int. Cl.[7] .............................. A61P 25/36; A61M 37/00
[52] U.S. Cl. ........................... 424/449; 424/493; 424/497
[58] Field of Search .............................. 424/484, 422–23, 424/434–435, 493, 497, 449, 461, 462, 469

[56] References Cited

U.S. PATENT DOCUMENTS

| | | |
|---|---|---|
| 4,626,539 | 12/1986 | Aungst et al. . |
| 5,149,538 | 9/1992 | Granger et al. . |
| 5,580,876 | 12/1996 | Crain et al. ............................. 514/282 |
| 5,587,381 | 12/1996 | Sinclair . |
| 5,767,125 | 6/1998 | Crain et al. . |
| 5,783,583 | 7/1998 | Simon . |
| 5,789,411 | 8/1998 | Gooberman et al. . |
| 5,811,451 | 9/1998 | Minoia et al. . |

OTHER PUBLICATIONS

Text—*Opioid Peptides in Substance Abuse* by Jozsef I. Szekely. CRC Press, Inc., p. 160 (1994).

Article—Spanagel et al.—"Opposing tonically active endogenous opioid systems modulate the mesolimbic dopaminergic pathway" *Proc. Natl. Acad. Sci. USA* vol. 89. p. 2046. Mar. 1992.

Article—Pan et al. "Cellular mechanism for anti–analgesic action of agonists of the k–opioid receptor" *Nature* vol. 389/25 Sep., pp. 382–385 (1997).

Article—Kreeks et al. "Orally Administered opioid antagonists reverse both mu and kappa opioid agonists delay of gastrointestinal transit in the guinea pig"*Life Sciences,* vol. 56. No. 14. pp. 1187–1192. 1995.

Article—Arts et al. "Inhibition of the Antianalgesic Action of Dynorphin A in Mice by Cholera Toxin" *Pharacology Biochemistry and Behavior,* vol. 46. pp. 623–629. 1993.

Article—Bakashi et al. "Dynorphin A–(1–17) Induces Alterations in Free Fatty Acids, Excitatory Amino Acids, and Motor Function Through An Opiate–Receptor–Mediated Mechanism" *The Journal of Neuroscience,* Dec. 1990. 10(12): 3793–3800.

Article—Behrmann et al. "A Comparison of YM–14673. U–50488H, and Nalmefene after Spinal Cord Injury in the Rat" *Experimental Neurology* 119. 258–267 (1993).

Article—Ohnishi et al. "Aquaretic Effect of the Stable Dynorphin–A analog E2078 in the Human" The Journal of Pharmacology and Experimental Therapeutics vol. 270. No. 1. Mar. 19, 1994.

*Primary Examiner*—Edward J. Webman
*Attorney, Agent, or Firm*—Steven J. Moore; Cummings & Lockwood

[57] ABSTRACT

Methods whereby a kappa-preferring opioid blocking agent is used for optimizing dopamine homeostasis during administration of opioid analgesics and for preventing mortal respiratory depression due to drug overdose.

10 Claims, No Drawings

SALTS AND BASES OF THE 17-(CYCLOPROPYLMETHYL)-4,5 ALPHA-EPOXY-6-METHYLENEMORPHINAN-3,14 DIOL MOLECULE FOR OPTIMIZING DOPAMINE HOMEOSTASIS DURING ADMINISTRATION OF OPIOID ANALGESICS

This application is a continuation-in-part of commonly owned, application, Ser. No. 08/631,081, filed Apr. 12, 1996 now U.S. Pat. No. 5,783,583, the disclosure of which is incorporated herein by reference.

FIELD OF INVENTION

The present invention relates to a method for optimizing dopamine levels in or out of the central nervous system during administration of exogenous opioid agonist drugs. The result of maintaining an optimal homeostasis of dopamine levels at specific sites in human organs enhances the "positive" effects of opioid agonist analgesics, namely euphoria, analgesia, and improved motor and behavioral functioning, such that a lesser amount of opioid agonist analgesic is necessary to produce a given effect of analgesia or euphoria, which in turn, reduces the risk for becoming chemically dependent upon opioid agonist analgesics.

"Positive" effects of opioid agonist analgesics are effects which are desirable and which are the intended effects associated with the administration of exogenous opioid agonists. Such positive effects include analgesia or pain relief, euphoria or feeling good, and calming so as to reduce heart rate, blood pressure or breathing rate. "Negative" effects of opioid agonist analgesics are effects that are undesirable and which are not the intended effects associated with administration of exogenous opioid agonists. Such negative effects include dysphoria, abnormal motor function, constipation, difficulty urinating and becoming chemically dependent upon the opioid agonist analgesics.

The 17-(cyclopropylmethyl)-4,5-alpha-epoxy-6-methylenemorphinan-3,14 diol molecule, also known as nalmefene, is generally classified as a kappa-receptor preferring, pure opioid antagonist. In the present invention, low doses of nalmefene are combined in structural preparations with an opioid agonist analgesic drug so as to increase the analgesic effect of, and to decrease the risk of chemical dependence to, said opioid agonist analgesic drug at therapeutic doses of opioid agonist. At doses greater than therapeutic for opioid agonist, the present invention will also tend to block positive effects of the opioid agonist, so as to dissuade the human from self-administering more opioid agonist than intended by a health professional. This is of very great importance because illicit abuse of opioid agonist analgesics by self-administration is a great societal problem which often leads to chemical dependency, addiction, ill health effects, crime, a burden on the criminal justice system, disruption of family well-being and many other bad outcomes.

BACKGROUND OF THE INVENTION

Opioid agonist analgesic drugs are generally administered to reduce or relieve pain. Examples of such drugs are morphine, meperidine, fentanyl, opium and hydrocodone. There are many other opioid agonist analgesic drugs to which the present invention applies.

Unfortunately, administration of an opioid agonist analgesic drug over a prolonged period of time, as common for treating many pain syndromes, generally results in the development of physiological tolerance to said opioid agonist analgesic drug, whereby an increasing amount of said opioid agonist analgesic drug is required over time to produce an equivalent analgesic effect. This may lead to chemical dependence upon the opioid agonist analgesic, whereby abrupt withdrawal of opioid agonist drug will produce physical signs and psychological symptoms that, in general, are opposite to those positive effects which the opioid agonist originally produced. Such withdrawal signs include excitation of the sympathetic nervous system such as release of norepinephrine from the locus coeruleus in the brain, increased heart rate and blood pressure, increased respiratory rate, altered gastrointestinal function leading to nausea, vomiting and/or diarrhea, piloerection ("goose bumps"), pain, and psychological or psychosomatic symptoms such as experiencing "hot and cold flashes," difficulty sleeping and chills. Abdominal cramps, aches and pains—especially cramping in the legs, and involuntary movement—especially kicking of the legs, and feeling weak are other complaints associated with withdrawal of opioid agonists from a human chemically dependent upon them. In general, this myriad of signs and symptoms is what is known colloquially as being "dope sick." It is this dope sickness that often is the incentive for humans chemically dependent upon opioid agonists to seek out and self-administer opioid agonist analgesic drugs without proper supervision by a medical professional. When other behavioral factors come into play, such as impairment of social functioning, criminal behavior to support use of the opioid agonist drug, and/or psychiatric or psychological deterioration directly attributable to the drug's use, the human is said to have an addiction to the opioid agonist analgesic. Common opioid agonist analgesics to which humans are often addicted include heroin, methadone and their derivatives. Humans have the potential to become addicted to many other opioid agonist analgesic drugs.

There has been a long-felt need to develop ways of delivering opioid agonist analgesic drugs without causing, or attenuating to the greatest degree possible, negative effects of said drugs at their therapeutically prescribed doses. This is accomplished by striking the optimal balance of effects between dopamine-increasing opioid receptors, such as mu-opioid receptors, and dopamine-decreasing opioid receptors, such as kappa-opioid receptors. The present invention fulfills this need in a unique and novel way that has not been appreciated by those skilled in the all of opioid analgesics.

The present author describes in the application for U.S. Pat. No. 5,783,583 in great detail the unique characteristics common only to the opioid antagonist nalmefene which set nalmefene apart from other opioid antagonists such as, for example, naloxone and naltiexone. U.S. Pat. No. 5,783,583 ('583) further describes how the unique opioid receptor subtype binding profile of nalmefene enables nalmefene alone, as compared to naloxone and naltrexone, to allow preferred antagonism of opioids at the kappa-opioid receptors versus the mu-opioid receptors, which in turn, results in an optimal homeostatic balance of dopamine.

Szekely (Exhibit A) shows a schematic representation of two opposing opioid systems located in the mesolimbic system of the human central nervous system. These systems modulate A10 dopaminergic neurons projecting in the nucleus accumbens. As illustrated in Exhibit A, stimulation of mu-opioid receptors (the mu subtype of opioid receptor) in the ventral tegmental area (VTA), the site of origin of the A10 neurons, increase dopamine release in the nucleus accumbens (NA). Selective blockade of this mu-receptor results in significant decrease in dopamine release in the nucleus accumbens. In stark contrast, stimulation of kappa-receptors (the kappa subtype of opioid receptor) in either the VTA or the NA results in a decrease in the amount of dopamine released. Selective blockade of kappa-receptors significantly increases dopamine release.

Spanagel et al. (exhibit B) demonstrate that tonically active and functionally opposing mu and kappa opioid systems regulate mesolimbic dopamine release in the nucleus accumbens. They report that the injection of mu-opioid agonists such as DAGO into the VTA stimulate mu-opioid receptors and increase the release of dopamine from the VTA into the NA. As would be expected, administration of a mu-opioid receptor antagonist into the VTA decreases dopamine release. The authors further report that kappa-opioid receptors agonists such as U-6953 infused into the NA inhibit dopamine release there, whereas kappa-opioid receptor antagonists such as nor-BNI increase dopamine release. An "agonist" is a "like" chemical with similar action to a given drug. An "antagonist" is a chemical, often with a similar chemical structure to a given drug, which exerts a dissimilar action to the given drug, in general preventing the "like" action of that given drug. With opioid receptors, in general, an agonist binds to the receptor and activates it in such a way as to begin a cascade of chemical or pharmacological events so as to result in the end effect related to a particular opioid receptor subtype. In contradistinction, an antagonist will bind to the receptor but not activate it. An antagonist exerts its actions by blocking the receptors from agonists, by physically occupying the space on the receptor where an agonist would otherwise bind.

The opposing mu and kappa opioid systems acting together provide a homeostasis of dopamine levels within the central nervous system. Changes in these opioid systems, such as by activation or blockade of the specific receptors, would therefore be expected to modulate opioid-induced effects that are mediated by mesolimbic pathways. Mu and kappa receptors are found elsewhere in the human body. For example, they have been located in the spinal cord (See Fujimoto, Bakshi and Behrmann, below) and in other non-central nervous system organs such as the kidney and intestine (See Ohnishi and Kreek, below). Accordingly, the model presented provides a neurochemical framework for understanding the adaptive changes resulting from long term use of opioids, as well as the clinical response elicited by exogenously administered opioid agonists and antagonists having different binding profiles.

For example, modifications in opioid-induced behavior resulting from changes in these mu and kappa systems are reported by Pan et al (Exhibit C). These authors state that the effects of opposing mu and kappa receptors extend to opioid action on emotion, perception and drug reinforcement. While morphine and other mu-opioid agonists increase dopamine release and produce euphoria and place preference, kappa-opioid agonists reduce mesolimbic dopamine release and produce dysplioria and aversion.

Scientists have shown that nalmefene, relative to other opioid antagonists such as naloxone and naltrexone, is significantly more kappa-receptor preferring. By way of example, Kreek et al. (Exhibit D) conclude that nalmefene has more kappa binding activity than either naloxone or naltrexone. Specifically, nalmefene is more potent than either naloxone or naltrexone as a kappa-receptor antagonist, and therefore would block kappa agonists (e.g. the naturally occurring dynorphin) to a greater extent than the other antagonists.

Fujimoto et al. (Exhibit E) demonstrate differences between mu and kappa receptor effects in the spinal cord. Specifically, these authors report that the administration of dynorphin, a potent kappa agonist, results in decreased analgesia. The dynorphin causes antianalgesic effects at the level of the spinal cord. Fujimoto shows that when a kappa-opioid receptor antagonist such as Cholera Toxin is given, the antianalgesic effect of dynorphin is inhibited.

Bakshi et al. (Exhibit F) shows that kappa receptors are widely distributed in the spinal cord, and that administration of dynorphin causes motor impairment. These authors also demonstrate that nalmefene is selective for these intraspinal kappa receptors, and limits dynorphin induced motor dysfunction after spinal cord injury.

Behrmann et al. (Exhibit G) report that a single dose of nalmefene has increased activity at kappa receptors and that a single dose of nalmefene exerts a significant neuroprotective effect after acute spinal cord injury, in direct contrast to the mu-preferring opioid antagonist naloxone that showed no significant effect on neurological recovery after spinal cord injury.

Ohnishi et al. (exhibit H) teach the effects on urine production due to kappa-opioid receptor pharmacology at both the level of the pituitary gland and the kidney.

'876 makes no mention of the positive and negative effects of opioid agonists taught in the present invention. For instance, no mention is made in '876 regarding euphoria versus dysphoria, or behavioral effects such as emotion, perception, drug reinforcement and place preference. Further, '876 does not address effects upon intestinal function or urination. Perhaps most convincingly, however, is that '876 makes no reference to the opposing mu and kappa opioid receptors in maintaining a homeostatic balance of dopamine in the mesolimbic region of the brain, in the spinal cord, or at other peripheral sites such as the intestine or kidney.

Other investigators have contemplated preparations of opioid agonists in combination with naloxone. However, as '583 clearly shows, nalmefene and naloxone are not analogous compounds. Therefore, the present invention would not be obvious to one skilled in the art simply because naloxone has previously been combined with opioid agonists. In fact, because of naloxone's opioid receptor subtype binding profile, it could not exert the positive opioid effects as nalmefene at similar doses, as taught in the present invention.

SUMMARY OF THE INVENTION

The present invention is directed to methods for magnifying the positive effects of opioid agonist analgesic drugs by effectively antagonizing kappa-opioid receptors to a much greater extent than mu-opioid receptors at recommended therapeutic doses, such that less opioid agonist will need to be administered for a given positive effect, thus decreasing the tendency for physiological tolerance to the drug, and hence decreasing the risk of chemical dependency or addiction, while also resulting in appreciable antagonism of mu-opioid receptors when the opioid agonist analgesic is administered at above the recommended therapeutic dose so as to dissuade a human being from self-administering excessive amounts of opioid agonist analgesic. The methods consist of administering to a living human being or animal a prescribed dose of nalmefene in combination with a prescribed dose of opioid agonist analgesic, the amount of nalmefene being effective to significantly antagonize kappa receptors while at the same time having minimal antagonistic effect on mu receptors, thus enhancing the positive effects of opioid agonists, such that the agonist actions by mu opioid agonists will far outweigh any antagonism by nalmefene at said mu-opioid receptors at recommended therapeutic doses.

The present invention also provides a structural composition comprising a therapeutic dose of opioid agonist analgesic in combination with an amount of nalmefene effective to enhance the positive effects of the opioid agonist analgesic, while at the same time exerting minimal antagonistic effects at mu-opioid receptors, when the opioid agonist analgesic is administered in recommended therapeutic doses, such that the agonist actions of the opioid agonist analgesic will far outweigh any antagonism by nalmefene at said mu-opioid receptors. If excessive amounts of the structural composition comprising nalmefene and opioid agonist analgesic are administered, enough nalmefene shall be administered as to begin to antagonize or block mu-opioid receptors from the exogenously administered opioid agonist analgesic in addition to kappa-opioid receptors, such the human being will be dissuaded from self administering such excessive amounts of said structural composition.

In summary, this present invention is directed to a method for optimizing the homeostatic control of dopamine release in the central nervous system (CNS) which will tend to enhance the analgesic effect of a selected opioid agonist analgesic at intended therapeutic doses of said opioid agonist analgesic, and which at doses higher than the intended therapeutic dose of opioid agonist analgesic will tend to exert undesirable effects so as to dissuade a human from self-administering greater than the intended therapeutic dose of said opioid agonist analgesic. The method comprises administering to a human or animal an opioid agonist analgesic and an amount of nalmefene or other similar kappa-preferring opioid antagonist in definite proportions, such that relatively lesser amounts of the proportioned nalmefene and opioid agonist analgesic will tend to optimize CNS dopamine levels thus enhancing analgesic and other desirable effects of the opioid agonist analgesic, and relatively greater amounts of the proportioned nalmefene and opioid agonist analgesic will tend to produce an adverse balance of CNS dopamine thus limiting positive or desirable effects of the opioid agonist analgesic, and therefore dissuade a human or animal from self-administering greater than the intended therapeutic dose of opioid agonist analgesic. The specific proportions of each, nalmefene and opioid agonist analgesic, will depend upon the potency of the particular opioid agonist analgesic, and pharmacokinetic profiles of the drugs, including volumes of distribution, elimination constants, blood half-lives, elimination half-lives, solubilities, binding to physiological proteins and so forth. In light of the present invention, one skilled in the art can compensate for these parameters. In general however, on a mass unit basis, the ratio of opioid agonist analgesic to nalmefene shall range from approximately 1.2:1 to 990:1.

OBJECT AND ADVANTAGES OF THE PRESENT INVENTION

Accordingly, besides the objects and advantages of combining nalmefene in a common carrier medium with an opioid agonist analgesic to form a structural composition for administration to a human being described in the present invention, some objects and advantages of the present invention are:

a) To administer opioid agonist analgesic medications in a smaller amount effective to produce the desired effects of the opioid analgesic medication; and, b) The aforementioned object and advantage "a" saves expensive resources in the manufacture of opioid agonist medications; and, c) The aforementioned object and advantage "a" reduces the rate at which tolerance to opioid agonist analgesic occurs, which results in a reduced risk for the development of chemical dependency and addiction; and d) To put an effective "ceiling" on the amount of opioid agonist medication that is likely to be self-administered by a human being—at excessively high amounts of the composition containing both nalmefene and opioid agonist analgesic, the amount of nalmefene administered will start to exert negative effects by antagonizing or blocking mu-opioid receptors in relation to the exogenously administered opioid agonist analgesic in addition to antagonizing or blocking kappa receptors; and e) The aforementioned object and advantage "d" greatly limits the potential for abuse of opioid agonist analgesics, which results in a reduced risk for the development of chemical dependency and addiction; and, f) To, with a single composition containing both nalmefene and opioid agonist analgesic, result in both of the aforementioned objects and advantages "a" and "d" at amounts of administered single composition which reasonably limit self-administration of very large doses of opioid agonist analgesic (as could not occur if the concentration of nalmefene in the single composition was less than in the present invention by orders of magnitude); and, g) To produce in an easy composition to administer, both nalmefene and opioid agonist analgesic, in amounts that when recommended therapeutic amounts of the composition are administered, nalmefene shall work in concert with the opioid agonist analgesic to produce the desirable effects of the opioid agonist analgesic drug, but which at higher amounts of composition will elicit undesirable effects; and, h) To produce a composition for administration, containing both nalmefene and an opioid agonist analgesic, such that release of the two drugs results in concentrations of nalmefene, relative to the opioid agonist analgesic, that will produce the intended effects as stated in the aforementioned object and advantage "g;" and, i) To greatly reduce the likelihood of mortal respiratory depression for a human or animal that is administered too high a dose of opioid agonist analgesic, either by mistake or by intention; and, j) To decrease the likelihood or severity of constipation in association with administration of an opioid agonist analgesic.

DETAILED DESCRIPTION OF THE PRESENT INVENTION

The present invention comprises the administration of nalmefene with an opioid agonist analgesic, in sufficient doses of nalmefene to, i) enhance the analgesic effect of the opioid agonist analgesic at recommended therapeutic doses of opioid agonist analgesic effective to produce positive effects such as relief of pain and euphoria, but which are not in excess of a recommended therapeutic dose of analgesic, and ii) produce undesirable effects at larger doses of opioid agonist analgesic which are in excess of the recommended therapeutic dose.

One embodiment of the present invention is a method whereby nalmefene and opioid agonist analgesic are administered by titration to a human being, using pain relief and euphoria as endpoints for desirable effects, and using dysphoria and the experiencing of pain as endpoints for undesirable effects. Titration of drugs may be of any acceptable method, such as, for example, by intravenous administration.

A more practical, and the preferred embodiment of the invention, is a composition comprising an opioid agonist analgesic medication and nalmefene, in amounts of each drug, such that when the composition is administered to yield a prescribed amount of administered opioid agonist analgesic, an amount of nalmefene is administered such that, i) at therapeutic doses of opioid agonist analgesic, an amount of nalmefene is administered which effectively blocks kappa-opioid receptors but which has minimal activity at mu-opioid receptors, and ii) at doses in excess of recommended therapeutic doses of opioid agonist analgesic, an amount of nalmefene is administered which appreciably blocks by competition mu-opioid receptors in relation to the exogenously administered opioid agonist analgesic.

The optimal amount of nalmefene to accomplish the objectives of the present invention will depend, in part, upon which opioid agonist analgesic is co-administered with nalmefene, as different opioid agonist analgesics have different potencies and different affinities for binding various opioid receptors at a given mass unit dose of opioid agonist, such as milligrams, micrograms or nanograms.

Ideally, the preferred embodiment of the invention matches an opioid agonist analgesic to nalmefene which has a similar pharmacokinetic properties, such as elimination half-live, as nalmefene, so that the concentrations of each drug remain in proper proportion relative to one another over time, and so one drug does not accumulate over time to a greater extent than the other drug, to an effect detrimental to the scope of the present invention. Where the opioid agonist half-life is significantly different from nalmefene, a time release formulation of either drug can be incorporated into the composition such that the pharmacokinetics of the two drugs become more compatible.

EXAMPLE 1

A recommended therapeutic dose of morphine, e.g. 0.15 mg/kg morphine, preferably in the form of morphine sulfate, is co-administered parenterally with 0.00025 to 0.0015 milligrams per kilogram (mg/kg) nalmefene, preferably in the form of nalmefene hydrochloride, more preferably 0.0007 mg/kg nalmefene. For a young adult 70 kg human, for example, 10.5 mg morphine sulfate is administered parenterally, along with 0.049 mg, or 49 micrograms (ug), nalmefene hydrochloride parenterally. This small amount of nalmefene, consistent with the present invention, will block, at least partially, kappa-opioid receptors. This same dose of nalmefene, consistent with the present invention, produces no appreciable effect at mu-opioid receptors in relation to the 10.5 mg dose of morphine. Thus, taking into account the binding affinities of nalmefene for different opioid receptors as described in '583, the present invention teaches that these doses of nalmefene and morphine will result in optimal levels of dopamine in the brain or spinal cord, thus enhancing the positive effects of morphine.

In a preferred embodiment of the present invention, morphine sulfate and nalmefene hydrochloride are co-existent in a common medium compatible for parenteral administration in the ratio of 0.15 mg active morphine to 0.0007 mg active nalmefene. Ideally, if administered subcutaneously, the total amounts of the two co-administered active drugs would be contained within an injectable volume of approximately 1 to 2 milliliters (cc) for a 70 kg adult human.

Assuming that 10.5 mg active morphine and 49 ug active nalmefene are contained within a 1.5 cc liquid vial, if a human self-administered twice the recommended therapeutic dose, i.e. 3 cc, then the human would receive 21 mg morphine and 98 ug nalmefene, or approximately 0.1 mg nalmefene. This amount of nalmefene would serve a protective effect to greatly decrease the likelihood that said human would succumb to a morphine overdose, such as life-threatening respiratory depression. Some investigators believe that respiratory depression is regulated by kappa-opioid receptors in a part of the brain not necessarily correlating with homeostasis of dopamine in the nucleus accumbens, the ventral tegmental area or the spinal cord. This amount of morphine and nalmefene administered together gives a ratio of morphine to nalmefene of approximately 214 to 1 on a unit mass basis.

If a human self-administered 10 times the recommended therapeutic dose of morphine, or 105 mg morphine, the invention embodied in this example would result in approximately 0.5 mg nalmefene being administered. This dose of nalmefene tends to significantly compete with the exogenously administered morphine, such that the mu-opioid blocking effect of nalmefene would tend to compete significantly with the mu-opioid activating effect of morphine, resulting in some negation of the desirable effects of the opioid agonist analgesic, resulting in a relative lack of pain relief. In addition to being highly protective against life-threatening drug overdose, the human would tend to be dissuaded from using 10 times the medium containing morphine and nalmefene in the ratio described in this example. Some investigators believe that respiratory depression is regulated by mu-2 opioid receptors.

If a high enough dose of the morphinelnalmefene preparation is administered, concentration of nalmefene at mu-receptors may become high enough so as to appreciably compete with endogenously produced beta-endorphin, thus eliciting negative effects such as dysphoria. This would additionally tend to dissuade the human from administering more of the preparation, or from repeating these series of events in the future.

EXAMPLE 2

Fentanyl is approximately 100 times as potent as morphine on a unit mass basis, e.g. per milligram or per microgram. In addition, depending on the amount administered, fentanyl may tend to be shorter acting as compared to morphine. Therefore, when fentanyl (in its citrate form or as another congener) and nalmefene are co-existent in a common medium compatible for parenteral administration, a ratio of 0.0015 mg active fentanyl to 0.0007 mg active nalmefene would have a similar compatibility profile as in example 1 immediately upon administration, i.e., before significant redistribution and elimination. However, because fentanyl is so relatively short-acting as compared to nalmefene, repeated administrations of a composition with this ratio of fentanyl to nalmefene may result in accumulation of nalmefene relative to fentanyl, such that fentanyl may become ineffective at mu-opioid receptors at a concentration of fentanyl that is not intended for this to occur. Therefore, a lower dose in the range of nalmefene consistent with this invention could be employed.

Fentanyl 0.0015 mg/kg and nalmefene 0.00025 mg/kg administered together gives a ratio of fentanyl to nalmefene of 15 to 2.5 on a unit mass basis. To a 70 kg young adult human being, 0.105 mg fentanyl (105 ug fentanyl) is co-administered with 0.0175 mg nalmefene (17.5 ug nalmefene). 105 ug fentanyl is a therapeutic dose to treat pain for a young adult human. 17.5 ug nalmefene would tend to have appreciable blocking effects at kappa-opioid receptors, because nalmefene is a kappa-preferring opioid antagonist. However, at mu-opioid receptors, this amount of nalmefene would not tend to compete effectively with endogenously produced beta-endorphin, and would also tend to be relatively inconsequential in competing with this amount of exogenously administered fentanyl at mu-receptors. Thus, the overall expected effect would be an enhancement of the positive effects of fentanyl.

If a human tried to self-administer, by way of example only, the stated therapeutic dose of the combined fentanyl/nalmefene preparation every one hour, yielding doses of fentanyl (alone, i.e. with no nalmefene) that cumulatively could produce life-threatening respiratory depression in a 70 kg adult human not tolerant to opioid agonist analgesics, or doses that might be self-administered by a tolerant or non-tolerant human to attain euphoria on a frequent basis, the following would occur. Nalmefene, by virtue of its significantly longer plasma half-live, longer elimination half life, and greater affinity for staying bound to opioid receptors as compared to fentanyl, would accumulate and increase its concentration relative to fentanyl such that eventually concentrations of nalmefene would be present at mu-opioid receptors to significantly compete with the exogenously administered fentanyl, such that the mu-opioid blocking effect of nalmefene would tend to compete significantly with the mu-opioid activating effect of the exogenously administered opioid agonist analgesic, fentanyl. This, in addition to preventing a mortal respiratory depression, would dissuade a human from self-administering this amount of the fentanyl preparation so frequently.

Alternatively, when two drugs with such different pharmacokinetic profiles are combined in one preparation, such as fentanyl and nalmefene, the shorting acting drug, e.g. fentanyl, call be prepared by encasing the drug particles as a microcapsule or covering it with a material, such as cellulose, lactic acid polymers or the like, so that its release into systemic circulation following release from a combination matrix will be delayed to more match the pharmacokinetic profile of the longer-acting drug, e.g. nalmefene. In light of the present invention, one skilled in the art could readily prepare such a preparation.

Another alternative is to formulate a transdermal delivery system, or a patch to be worn on the skin of a human, which contains both fentanyl and nalmefene in proportions consistent with the present invention. There exists in the prior art a transdermal preparation for fentanyl, the Duragesic® patch. However, a significant problem exists with this product in that drug addicts are know to boil the patch in a solvent solution and then distill the solution to obtain a fentanyl preparation which can be readily abused by injecting it intravenously into a human. One preferred embodiment of the present invention involving a skin patch would be to formulate a patch with two drug delivery rates. Fentanyl could be delivered faster by being contained in an adhesive matrix that might be delivered by diffusion along a concentration gradient. The nalmefene could be delivered more slowly by using a partially permeable membrane that limits the transfer of nalmefene across the membrane. Thus the fentanyl and nalmefene are contained within two different compartments within the patch—fentanyl in the adhesive matrix, and nalmefene in a reservoir which is separated from the fentanyl by a partially permeable membrane. One skilled in the art, in light of the present invention may prepare other structures accomplishing the same goal. The partially permeable membrane may be temperature sensitive so that it degrades at a certain specified temperature, or made to degrade upon exposure to certain solvents. In this way, if the skin patch containing fentanyl and nalmefene were washed or boiled in a solvent, the nalmefene would be mixed with the fentanyl, in effect releasing nalmefene in amounts to significantly compete with the exogenously administered opioid agonist analgesic, fentanyl, at mu-receptors. This would tend to dissuade the human from repeating this act in the future. Thus, illicit abuse of transdermal fentanyl could be easily prevented, while at the same time allowing for a fentanyl/nalmefene skin patch that is highly effective in producing desirable effects and pain relief.

EXAMPLE THREE

Methadone is a relatively long-acting, orally administered opioid agonist analgesic, which is quite often used as a substitute for heroin in the treatment of humans addicted to heroin. One significant problem with methadone, however, is its high potential for illicit abuse. So high is this potential, that in the United States, methadone is typically distributed only in specified methadone dispensaries specially licensed by state agencies and the federal Drug Enforcement Agency. An embodiment of the present invention solves a long-sought need to formulate methadone in such a way as to i) optimize its action such that less drug is needed—this will slow down the process by which a human may become tolerant to methadone's effects, and ii) yield a form of drug that when misused will result in unpleasant side effects.

Nalmefene is known to undergo extensive first-pass metabolism in the liver. Because of this, orally administered nalmefene is roughly bioequivalent to 1/20 to 1/25 of intravenously administered nalmefene. Stated differently, 50 mg of nalmefene orally administered into the gastrointestinal track of a human will be approximately equivalent to 2 mg of nalmefene administered intravenously.

Some humans addicted to opioid agonist analgesics are known to be prescribed a liquid oral preparation of methadone, and if not properly supervised, inject in intravenously in order to attempt to get more of a "drug rush." To greatly decrease the likelihood of this misuse, a therapeutic dose of methadone in an oral preparation, for example 100 mg, is prepared by combining it with 1 mg of nalmefene (1 mg of nalmefene orally administered into the gastrointestinal tract is bioequivalent to approximately 40 ug, or 0.040 mg, of intravenously administered nalmefene). The ratio of methadone to nalmefene on a mass unit basis is 100 to 1 in this methadone/nalmefene preparation. Upon the intended oral administration of this combination of methadone and nalmefene, the nalmefene will tend to block kappa-receptors, optimizing the homeostatic balance of dopamine in the central nervous system, without having an appreciable effect on competition with endogenous endorphins at mu-opioid receptors, and having little, if any, substantial effect in competing with methadone at mu-receptors. Thus, the intended effect of methadone will be realized when administered per os. However, if a human self-administers this same preparation by intravenous route, then enough nalmefene will be present at mu-receptors to substantially compete with the exogenously administered opioid agonist analgesic, methadone. As such, the human will not experience the expected "drug rush," and may experience other undesirable effects as well, and therefore will be dissuaded from taking such action in the future, such as injecting intravenously a drug preparation intended for oral use.

EXAMPLE FOUR

Sufentanyl is a derivative of fentanyl that on a mass unit basis is 5 to 10 times as potent as fentanyl, or approximately 500 times as potent as morphine. When salts or bases of sufentanyl and nalmefene are co-existent in a common medium compatible for parenteral administration consistent with the present invention, a ratio of approximately 0.00030 mg active sufentanyl to 0.00025 mg active nalmefene may be administered. This, on a mass unit basis yields, a ratio of sufentanyl to nalmefene of approximately 1.2 to 1.

A typical therapeutic parenteral dose of sufentanyl to produce analgesia for a chronic pain syndrome in a young adult 70 kg human is approximately 21 ug. Therefore, approximately 18 ug nalmefene would be co-administered in a common composition with 21 ug sufentanyl. This amount of nalmefene would tend to optimize CNS dopamine as previously described. If 20 times the recommended therapeutic dose of sufentanyl were intravenously self-administered by a human, as for instance in an intentional suicide attempt, 420 ug of sufentanyl would be administered along with approximately 360 ug nalmefene. This amount of nalmefene would tend to substantially compete with that amount of exogenously administered opioid agonist analgesic sufentanyl at mu-2 opioid receptors and at kappa receptor to prevent mortal respiratory depression due to drug overdose.

EXAMPLE 5

10 mg of parenteral (subcutaneous) morphine is roughly equivalent in analgesic effect as 90 mg parenteral (subcutaneous) meperidine. Thus, meperidine has approximately one ninth the analgesic effect as the same amount of morphine on a mass unit basis. Therefore, a recommended therapeutic dose of meperidine, e.g. approximately 90 mg parenteral meperidine, is co-administered parenterally with 0.00025 to 0.0015 milligrams per kilogram (mg/kg) nalmefene, preferably in the form of nalmefene hydrochloride, more preferably 0.0013 mg/kg nalmefene. For a young adult 70 kg human, for example, approximately 90 mg meperidine is administered parenterally, along with 0.091 mg, or 91 micrograms (ug), nalmefene hydrochloride parenterally. This small amount of nalmefene, consistent with the present invention, will block, at least partially, kappa-opioid receptors. This same dose of nalmefene, consistent with the present invention, produces minimal effect at mu-opioid receptors in relation to the 90 mg dose of meperidine, and even less of a competitive effect relating to the endogenous beta-endorphin. Thus, taking into account the binding affinities of nalmefene for different opioid receptors as described in '583, the present invention teaches that these therapeutic doses of nalmefene and meperidine will result in levels of dopamine in the brain or spinal cord that will not appreciably result in undesirable effects. In fact, it is theoretically possible that the dose of nalmefene relative to the dose of meperidine may actually tend to avoid an unpleasant side effect of an opioid agonist analgesic administered alone, that is constipation. In other words, meperidine will exhibit a typical analgesic effect, but perhaps with less of a tendency to cause constipation. However, if 10 times the amount of meperidine is administered, by intention or mistake, then almost 1 mg of nalmefene will be administered. One milligram of nalmefene will definitely prevent mortal respiratory depress ion under these conditions, and will also considerably contribute to dissuading a human from self-administering an equal amount of the combined meperidine/nalmefene preparation in the future. On a mass unit basis, in this embodiment, the ratio of meperidine to nalmefene is approximately 990 to 1.

Though not necessarily the most preferred embodiment of the present invention, this fifth example nevertheless is perfectly suitable for dissuading a human from self-administering excessive doses of opioid agonist analgesic, as well as preventing mortal respiratory depression.

These five stated examples are in no way intended to limit the scope of the present invention, rather, by way of example only, are intended to understandably communicate the utility of the present invention by showing embodiments of how the invention may actually be used. It is to be understood that these stated embodiments are merely illustrative of various aspects of the present invention. It is further understood that modifications and other preparations may be devised without departing from the spirit and scope of the present invention.

For instance, nalmefene an d opioid agonist analgesics for use in the present invention may be in the form of free bases or pharmacologically acceptable salts thereof. Examples of suitable acids for salt formation, by way of example only, include but are not limited to hydrochloric acid, glucuronic acid, citric acid and so forth.

The opioid agonist analgesic and nalmefene may be administered to a human or animal by any of known methods such as, but not limited to, intramuscular, intravenous, nasal, oral, sublingual or transdermal methods.

For transdermal preparations, any of known permeation enhancers suitably compatible with patch ingredients may be used. A partially permeable barrier may separate the nalmefene and opioid agonist analgesic to control the release of the longer acting component to better match the physiological actions of nalmefene with those of the opioid agonist analgesic.

When the opioid agonist analgesic is significantly shorter-acting in duration than nalmefene, it may be prepared in a sustained release form by any of known methods, which in light of the present invention, would be apparent to one skilled in the art. Likewise, if nalmefene has a shorter in vivo life span than the opioid agonist analgesic, as in the case of LAAM (levo-alpha-acetylmethadol), the nalmefene may be prepared in such a sustained release form. One such sustained release form, which may be applicable in this instance, is the sustained release preparation used for dextromethorphan and marketed in the United States as Delsym®.

Other kappa-preferring opioid receptor antagonists may be used consistent with the present invention.

What is claimed in the present invention:

1. A method of administering opioid agonist analgesics to humans and animals comprising:

administering a therapeutic dose of an opioid agonist analgesic; and administering nalmefene in an amount sufficient to inhibit binding of the opioid agonist analgesic at kappa-opioid receptors with only minimal antagonism of the agonist analgesic at mu-opioid receptors.

2. The method of claim 1, wherein step (b) is further characterized in that the the nalmefene is administered in an amount which substantially blocks binding of the opioid agonist analgesic at mu-opioid receptors at doses of the agonist exceeding the therapeutic dose.

3. The method of claim 1, wherein steps (a) and (b) are performed simultaneously.

4. The method of claim 1, wherein the opioid agaonist analgesic and the nalmefene are administered via a transdermal patch.

5. A method for providing homeostasis of dopamine levels in humans or animals receiving opioid agonist analgesics, comprising:

administering a therapeutic dose of an opioid analgesic agonist and an amount of nalmefene to enhance the effects of dopamine-increasing opioid receptors and reduce the effects of dopamine-decreasing opioid receptors.

6. The method of claim 5, wherein the step of administering is further characterized in that the nalmefene antagonizes the dopamine-decreasing opioid receptors to a substantially greater extent than the dopamine-increasing opioid receptors.

7. The method of claim 6, wherein the dopamine-increasing opioid receptors are mu-opioid receptors and the dopamine-decreasing opioid receptors are kappa-opioid receptors.

8. The method of claim 6, wherein the amount of the nalmefene administered increases as the dosage of the opioid agonist analgesic exceeds the therapeutic dose.

9. The method of claim 5, wherein the administration of the nalmefene reduces the therapeutic dosage of the opioid agonist analgesic required to provide a therapeutic effect.

10. The method of claim 5, wherein the opioid agonist analgesic and the nalmefene are administered simultaneously.

* * * * *